US006881766B2

(12) United States Patent  
Hain

(10) Patent No.: US 6,881,766 B2
(45) Date of Patent: Apr. 19, 2005

(54) SUTURES AND COATINGS MADE FROM THERAPEUTIC ABSORBABLE GLASS

(75) Inventor: Matthew Hain, Wayne, NJ (US)

(73) Assignee: Tyco Healthcare Group LP, Norwalk, CT (US)

( * ) Notice: Subject to any disclaimer, the term of this patent is extended or adjusted under 35 U.S.C. 154(b) by 14 days.

(21) Appl. No.: 10/361,913

(22) Filed: Feb. 7, 2003

(65) Prior Publication Data

US 2004/0162580 A1 Aug. 19, 2004

Related U.S. Application Data

(63) Continuation of application No. PCT/US01/23526, filed on Jul. 26, 2001.
(60) Provisional application No. 60/225,906, filed on Aug. 17, 2000.

(51) Int. Cl.[7] .............................................. A61L 17/06
(52) U.S. Cl. ...................... 523/105; 523/122; 606/230; 606/231; 424/426; 424/443; 424/444; 424/446
(58) Field of Search ................................ 424/426, 443, 424/444, 446; 523/105, 122; 606/230, 231

(56) References Cited

U.S. PATENT DOCUMENTS

| 2,668,162 A | 2/1954 | Lowe et al. |
| 2,703,316 A | 3/1955 | Schneider et al. |
| 2,758,987 A | 8/1956 | Saizber et al. |
| 3,225,766 A | 12/1965 | Baptist et al. |
| 3,297,033 A | 1/1967 | Schmitt et al. |
| 3,422,181 A | 1/1969 | Chirgwin |
| 3,531,561 A | 9/1970 | Trehu |
| 3,565,077 A | 2/1971 | Glick |
| 3,565,869 A | 2/1971 | DePraspero |
| 3,620,218 A | 11/1971 | Schmitt et al. |
| 3,626,948 A | 12/1971 | Glick et al. |
| 3,636,956 A | 1/1972 | Schneider |
| 3,674,901 A | 7/1972 | Shepard et al. |
| 3,705,938 A | 12/1972 | Hyman et al. |
| 3,736,646 A | 6/1973 | Schmitt et al. |
| 3,772,420 A | 11/1973 | Glick et al. |
| 3,773,919 A | 11/1973 | Boswell et al. |
| 3,792,010 A | 2/1974 | Wasserman et al. |
| 3,797,499 A | 3/1974 | Schneider |
| 3,839,297 A | 10/1974 | Wasserman et al. |
| 3,867,190 A | 2/1975 | Schmitt et al. |
| 3,878,284 A | 4/1975 | Schmitt et al. |
| 3,982,543 A | 9/1976 | Schmitt et al. |
| 3,987,797 A | 10/1976 | Stephenson |
| 4,024,871 A | 5/1977 | Stephenson |
| 4,027,676 A | 6/1977 | Mattei |
| 4,047,533 A | 9/1977 | Perciaccante et al. |
| 4,060,089 A | 11/1977 | Noiles |
| 4,137,921 A | 2/1979 | Okuzumi et al. |
| 4,157,437 A | 6/1979 | Okuzumi et al. |
| 4,190,720 A | 2/1980 | Shalaby |
| 4,201,216 A | 5/1980 | Mattei |
| 4,234,775 A | 11/1980 | Wolfberg et al. |
| 4,237,920 A | 12/1980 | Norman |
| 4,300,565 A | 11/1981 | Rosensaft et al. |
| 4,517,006 A | 5/1985 | Drake et al. ............... 71/64.11 |
| 4,523,591 A | 6/1985 | Kaplan et al. |
| 4,582,052 A | 4/1986 | Dunn et al. |
| 4,605,730 A | 8/1986 | Shalaby et al. |
| 4,612,337 A | 9/1986 | Fox, Jr. et al. |
| 4,612,923 A | 9/1986 | Kronenthal |
| 4,624,256 A | 11/1986 | Messier et al. |
| 4,700,704 A | 10/1987 | Jamiolkowski et al. |
| 4,705,820 A | 11/1987 | Wang et al. |
| 4,711,241 A | 12/1987 | Lehmann |
| 4,788,979 A | 12/1988 | Jerrett et al. |
| 4,791,929 A | 12/1988 | Jerrett et al. |
| 4,994,074 A | 2/1991 | Bezwada et al. |
| 5,019,096 A | 5/1991 | Fox, Jr. et al. |
| 5,032,638 A | 7/1991 | Wang et al. |
| 5,047,048 A | 9/1991 | Bezwada et al. |
| 5,049,139 A | 9/1991 | Gilchrist ..................... 604/265 |
| 5,100,433 A | 3/1992 | Bezwada et al. |
| 5,290,544 A | 3/1994 | Shimono et al. |
| 5,330,770 A | 7/1994 | Kuno |
| 5,352,515 A | 10/1994 | Jarrett et al. |
| 5,413,788 A | 5/1995 | Edwards et al. |
| 5,470,585 A | 11/1995 | Gilchrist ..................... 424/604 |
| 5,534,288 A | 7/1996 | Gruskin et al. |
| 5,614,006 A | 3/1997 | Algar ..................... 106/18.31 |
| 5,744,151 A | 4/1998 | Capelli |
| 5,766,611 A | 6/1998 | Shimono et al. |
| 6,210,703 B1 | 4/2001 | Novich ..................... 424/443 |
| 6,482,444 B1 | 11/2002 | Bellantone et al. |
| 6,645,483 B1 | 11/2003 | McGhee ..................... 424/78.08 |

FOREIGN PATENT DOCUMENTS

| EP | 0328421 | 2/1989 |
| EP | 0633032 | 6/1994 |
| EP | 0647452 | 10/1994 |
| GB | 2079152 | 5/1981 |
| GB | 2 099 702 | 12/1982 |
| GB | 2146531 | 4/1985 |
| WO | 96/24364 | 8/1996 |
| WO | 9624364 | 8/1996 |
| WO | 9844965 | 10/1998 |
| WO | 9854104 | 12/1998 |
| WO | 00/47245 | 8/2000 |
| WO | 0047245 | 8/2000 |
| WO | 0128601 | 10/2000 |

OTHER PUBLICATIONS

Abstract JP 5–001226(Jan. 1993).

Primary Examiner—Margaret G. Moore

(57) ABSTRACT

Sutures fabricated from and/or coated with compositions including water-soluble glass are described herein. Pledgets containing water-soluble glass within the interstices of the pledget and/or coated with compositions including water-soluble glass are also described herein. The water-soluble glass optionally includes a therapeutic agent, e.g., silver to promote wound repair.

75 Claims, 2 Drawing Sheets

US 6,881,766 B2

SUTURES AND COATINGS MADE FROM THERAPEUTIC ABSORBABLE GLASS

This application is a continuation of PCT/US01/23526, filed Jul. 26, 2001, which claims priority to provisional application US No. 60/225,906, filed Aug. 17, 2000.

BACKGROUND

1. Technical Field

The present disclosure relates to sutures and more particularly to sutures made from, incorporating and/or coated with compositions of therapeutic absorbable glass. The present disclosure also relates to pledgets coated with compositions of therapeutic absorbable glass.

2. Description of Related Art

Antimicrobial agents have been associated with surgical devices to prevent contamination with germs. For example, U.S. Pat. No. 5,019,096 to Fox, Jr. et al. describes applying a coating to a medical device, the coating containing a matrix polymer and antimicrobial agents. Other examples of antimicrobial devices include U.S. Pat. Nos. 3,674,901; 3,705,938; 3,987,797; 4,024,871; and 4,612,337.

Sutures prepared from biocompatible bioabsorbable polymers are well known in the art and are described e.g., in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; 4,523,591, U.K. Patent No. 779,291; Gilding et al., *Biocompatibility of Clinical Implant Materials*, Vol. II, ch. 9: "Biodegradable Polymers" (1981). Synthetic biocompatible bioabsorbable multifilament sutures such as DEXON®, VICRYL®, and POLYSORB® commercially available from Ethicon, Inc. (Somerville, N.J.) and United States Surgical (Norwalk, Conn.) are well known in the industry.

Examples of biocompatible non-bioabsorbable polymers useful for fabricating sutures include, but are not limited to, nylon, silk, polyester, polypropylene, polyethylene, cotton, linen, etc. Commercially available sutures fabricated from biocompatible non-bioabsorbable polymers, e.g., a polyester suture (SURGIDAC®, United States Surgical, Norwalk, Conn.) and a polyester braided suture (TICRON®, David & Geck, Danbury, Conn.) are also well known in the industry.

Suture coating compositions are also well known in the art. For example, U.S. Pat. No. 4,027,676 describes an absorbable coating composition for sutures. Other suture coatings are described, e.g., in U.S. Pat. Nos. 4,624,256; 4,190,720; 4,582,052; 4,605,730; 4,700,704; 4,705,820; 4,788,979; 4,791,929; 4,994,074; 5,047,048; 5,100,433; 5,352,515; 5,032,638; 4,711,241; 4,705,820; and 4,201,216.

Water-soluble glasses have been utilized for a variety of medical, cosmetic and other purposes. For example, UK Patent Specifications Nos. 1,565,906, 2,079,152, 2,077,585 and 2,146,531, describe the dissolution of glasses impregnated with various agents such as drugs, hormones, insecticides, spermicides, and fungicides to provide controlled release of these agents. The glass can be in the form of an implant or bolus. WO 98/44965, describes a water-soluble biodegradable glass composition containing various active agents, e.g., antimicrobials such as antibiotics and metal compounds, e.g., silver oxide, silver orthophosphate, steroids, painkillers, etc., which is used for implantation in soft tissue.

WO 96/24364, describes a controlled release glass having various metals, e.g., silver, copper, and zinc useful for combating infections.

WO 98/54104, describes the preparation of water-soluble glass fibres which optionally contain silver compounds. The glass fibres are utilized in undefined orthopaedic implants and tissue engineering applications.

U.S. Pat. No. 5,470,585, describes the use of medicinal substances for topical applications, e.g., wound dressings, which include a water-soluble glass containing a silver compound.

U.S. Pat. No. 4,612,923 is directed to glass-filled absorbable surgical devices made of a synthetic absorbable polymer containing an absorbable glass filler.

U.S. Pat. Nos. 5,290,544 and 5,766,611, describe cosmetic products containing soluble glass which contains silver, copper or zinc ions having antibacterial activity. U.S. Pat. No. 5,330,770, describes a boron-free water-soluble glass containing silver oxide useful as a water treating agent.

While the aforementioned references describe the use of water-soluble glass for certain implant and cosmetic applications, wound dressings, treating infections, and water-treating agents there is no indication in the references of water-soluble glass-based coating compositions for sutures or pledgets, or sutures manufactured from water-soluble glass, which provide controlled, sustained release of a therapeutic agent.

SUMMARY

Figure 1A:
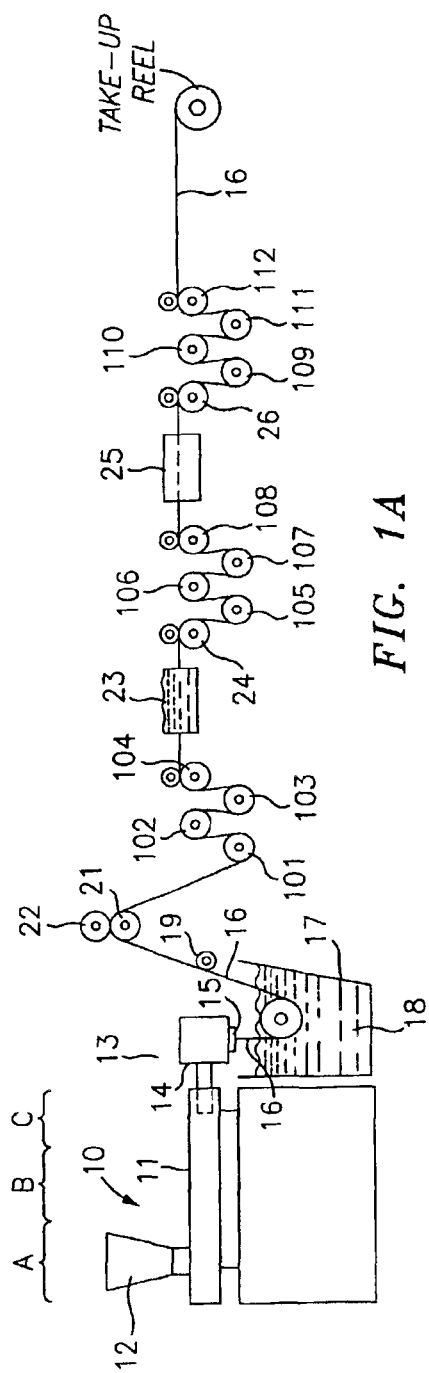
FIG. 1A is a schematic illustration of an apparatus which is suitable for manufacturing monofilament sutures.

A coating composition for a surgical device is provided which includes therapeutic water-soluble glass and a polymer selected from the group consisting of biocompatible bioabsorbable polymer and biocompatible non-bioabsorbable polymer wherein the coating composition is adapted to coat the surgical device.

A suture coated with a coating composition is also provided wherein the coating composition includes therapeutic water-soluble glass and a polymer selected from the group consisting of biocompatible bioabsorbable polymer and biocompatible non-bioabsorbable polymer.

A monofilament suture is also provided which includes therapeutic water-soluble glass, and a polymer selected from the group consisting of biocompatible bioabsorbable polymer and biocompatible non-bioabsorbable polymer.

A multifilament suture is also provided which includes filaments fabricated from biocompatible water-soluble glass.

A method for preparing a suture having therapeutic activity is also provided which includes applying to the suture a coating composition including a water-soluble glass including a therapeutically effective amount of a therapeutic agent.

A method of preparing a coating composition for a surgical device is also provided which includes dispersing therapeutic water-soluble glass in a polymer selected from the group consisting of biocompatible bioabsorbable polymer and biocompatible non-bioabsorbable polymer wherein the coating composition is adapted to coat the surgical device.

A pledget is also provided which incorporates water-soluble glass. In one aspect therapeutic water-soluble glass is contained within the interstices of the pledget. In another aspect, the water-soluble glass is coated onto the pledget and also contained within the interstices of the pledget. In yet another aspect, a pledget coated with a coating composition is also provided wherein the coating composition includes therapeutic water-soluble glass.

A method for preparing a pledget having therapeutic activity is also provided which includes applying to the pledget a coating composition including a water-soluble glass including a therapeutically effective amount of a therapeutic agent.

DESCRIPTION OF THE PREFERRED EMBODIMENTS

Described herein are sutures fabricated from water-soluble glass, coating compositions including water-soluble glass which are adapted for coating surgical devices, e.g., sutures and pledgets, and sutures and pledgets coated with such compositions. The incorporation of water-soluble glass containing a therapeutic agent (also known herein as therapeutic water-soluble glass) in association with sutures and surgical device coatings herein provides a unique sustained release dosage form at precisely defined locations within a body. In one aspect, a monofilament suture is provided which includes therapeutic water-soluble glass and a polymer selected from the group consisting of biocompatible bioabsorbable polymer and biocompatible non-bioabsorbable polymer. In this aspect, the suture may have incorporated into it therapeutic water-soluble glass. Alternatively, the suture may be coated with a composition incorporating therapeutic water-soluble glass. It should be understood that a suture incorporating therapeutic water-soluble glass can also be coated with a composition containing water-soluble glass. In another aspect, a multifilament suture is provided which includes filaments fabricated from water-soluble glass. Thus, in one embodiment, a multifilament suture is provided which is made of water-soluble glass. In another embodiment, the multifilament suture includes individual filaments fabricated from a combination of water-soluble glass and biocompatible bioabsorbable polymer or biocompatible non-bioabsorbable polymer. In another embodiment, the multifilament suture includes filaments fabricated from water-soluble glass and filaments fabricated from a combination of water-soluble glass and biocompatible bioabsorbable polymer or biocompatible non-bioabsorbable polymer. In another embodiment, the multifilament suture includes individual filaments fabricated from water-soluble glass and individual filaments fabricated from a biocompatible bioabsorbable polymer or biocompatible non-bioabsorbable polymer. In yet another aspect, a coating composition for a surgical device is provided which is prepared from biocompatible non-bioabsorbable or biocompatible bioabsorbable polymer and therapeutic water-soluble glass wherein the coating composition is adapted to coat the surgical device. In yet another aspect, a method for preparing the foregoing coating composition for a surgical device is provided which involves dispersing water-soluble glass in biocompatible bioabsorbable polymer or biocompatible non-bioabsorbable polymer wherein the coating composition is adapted to the surgical device. In yet another aspect, therapeutic water-soluble glass is incorporated in a pledget to provide a pledget having therapeutic activity. In one embodiment, the water-soluble glass is coated onto the pledget. In another embodiment, the therapeutic water-soluble glass is contained within the interstices of the pledget. In another embodiment, a pledget is provided which contains water-soluble glass within the interstices of the pledget and which is coated with water-soluble glass. In yet another embodiment, the pledget is coated with a coating composition, the coating composition including a therapeutic water-soluble glass. As used herein, the terms "include, includes and including" are intended to mean "incorporating, but not limited to."

Water-soluble glass (a.k.a. "absorbable glass") is incorporated in all aspects and embodiments herein. While glass, in general, is a durable material, the structure of glass can be made soluble in water and body fluids mainly by the addition of glass modifiers. The rate of dissolution of the water-soluble glass in water and body fluids can be arbitrarily controlled as described below. Thus, incorporation of therapeutic agents into water-soluble glass (therapeutic water-soluble glass) provides a vehicle for gradual release of desired therapeutic agents from the glass as the glass dissolves. Accordingly, sutures containing water-soluble glass and sutures and pledgets coated with compositions including a water-soluble glass can provide controlled, sustained release of a therapeutic agent over a selected period of time ranging from minutes to weeks or longer.

Water-soluble glasses are well-known in the art and are described, e.g., in U.S. Pat. Nos. 5,330,770, 5,290,544, 5,470,585 and WO98/44965, each being incorporated herein by reference. Typically, water-soluble glasses are made of one or two glass-forming oxides also known as glass formers, e.g., silicon dioxide, boric oxide, and phosphorus pentoxide in combination with one or more of glass modifiers such as calcium oxide, sodium oxide, potassium oxide, zinc oxide, barium oxide, magnesium oxide, and mixtures thereof. For example, aforesaid U.S. Pat. No. 5,330,770, describes a boron-free water-soluble glass manufactured from a silicon dioxide as the glass former, and sodium oxide as the glass modifier. Silver oxide is incorporated into the water-soluble glass as an antibacterial agent. Aforesaid U.S. Pat. No. 5,290,544, describes a water-soluble glass including silicon dioxide or phosphorus pentoxide as the glass former and calcium oxide, potassium oxide or sodium oxide as the glass modifier. The glass further includes at least one metal ion such as $Ag^+$, $Cu^+$ and $Zn^{2+}$ having an antibacterial property. Aforesaid U.S. Pat. No. 5,470,585 and WO 98/44965, describe a water-soluble glass including phosphorous pentoxide as the principal glass former, and various glass modifiers, e.g., potassium oxide, magnesium oxide, zinc oxide and calcium oxide. Water-soluble glasses are also commercially available, e.g., ARGLAES® glass (Giltech Limited, Great Britain). Water-soluble glasses utilized in accordance with this disclosure are biocompatible which means that the glasses do not elicit substantially adverse affects, e.g., undue toxicity or undue irritation, when implanted into living tissue.

The composition of the water-soluble glass can be specifically formulated to achieve a particular dissolution rate. The rate of dissolution is controlled by the ratio of glass modifier to glass former and by the relative amount of the glass modifiers in the glass. Generally, the glass dissolution rate decreases as the concentration of modifier increases. The glass dissolution rate of the water-soluble glass utilized in this disclosure may typically range from about 0.1376 to 2500 $mg/cm^2$, while dissolution rates ranging from about 0.1376 to about 16.4549 $mg/cm^2$ are more desirable.

The water-soluble glass can be produced by conventional methods well known in the art. Typically, the glass is prepared by combining the components, i.e., glass former and glass modifiers and optionally a therapeutic agent as described below, in a platinum or aluminum crucible and heating the mixture at a temperature ranging from about 1000° to about 1200° C., and preferably at 1100° C. for about one to about four hours. The molten glass is then cooled and pulverized to a fine particle size or coarse granules or pellets by, e.g., ball milling, air jet milling, etc. The glass particle size may generally range from about 1 to about 50 microns, and more preferably from about 6.5 to about 25.44 microns.

As mentioned above, a therapeutically effective amount of a therapeutic agent may be incorporated into the water-soluble glass which is delivered at a desired site upon dissolution of the glass. Therapeutic agent refers to one or more medico-surgically useful substances, e.g., those which accelerate or otherwise beneficially augment and/or aid the natural healing process when applied to injured or diseased tissue. A therapeutic agent herein may generally be incorporated into water-soluble glass during manufacture. Accordingly, one skilled in the art will appreciate that useful therapeutic agents herein should not be adversely affected by the glass-manufacturing process, i.e., they will remain biologically active. Suitable therapeutic agents include, but are not limited to, antimicrobial agents such as metals including copper, silver, zinc, magnesium, cerium, manganese, bismuth, selenium and boron, antibiotics including bactericidal, fungicidal, and infection-preventing drugs such as, e.g., gentamicin, vancomycin, penicillin, and cephalosporins; growth factors to provide wound repair and/or tissue growth such as insulin-like growth factors I and II, macrophage derived growth factor, alveolar derived growth factor, growth hormone, fibroblast growth factor, platelet derived growth factor; transforming growth factor-beta, etc.; osteogenic factors such as bone morphogenetic proteins and peptides, hormones such as estrogen, calcitonin, parathyroid hormone, vitamin and mineral supplements with calcium, phosphate, vitamin D, etc., bone chips and the like; anti-inflammatory agents; analgesics; immunosuppressants; other drugs and combinations thereof. Water-soluble glasses containing metals, e.g., silver, are particularly well-suited to remaining unchanged during the glass manufacturing process and are efficacious in minimizing bacterial infections. Therapeutically effective amounts of particular therapeutic agents are well-known to those skilled in the art.

When the therapeutic agent is a metal, it is introduced into the glass, preferably, in the form of a salt during manufacture of the glass as described, e.g., in U.S. Pat. No. 5,871,777 or WO 96/24364, the contents of each of which are incorporated herein by reference, and in U.S. Pat. No. 5,470,585. For example, silver can be incorporated into water-soluble glass in the form of silver oxide, silver nitrate and silver orthophosphate.

The amount of therapeutic agent utilized in the water-soluble glass will depend on the conditions of use and the desired rate of release from the glass. A therapeutically effective amount of a therapeutic agent is the amount necessary to achieve desired minimal therapeutic activity. Typically, the amount of therapeutic agent can range from about 0.5 to about 50 mole percent depending on the potency of the agent. The higher the concentration of therapeutic agent contained in the glass, the higher the amount of the agent's release. In addition, by controlling the speed of glass dissolution, more or less therapeutic activity may be achieved. Faster dissolution results in more rapid release of the therapeutic agent. When using silver as the therapeutic agent, e.g., in the form of silver oxide, the amount of therapeutic agent typically ranges from about 0.1 to about 10 mole percent, and preferably from about 1.0 to about 5.0 mole percent. As used herein therapeutic water-soluble glass refers to water-soluble glass as defined herein having a therapeutically effective amount of a therapeutic agent.

As mentioned above, bioabsorbable polymers and non-bioabsorbable polymers are utilized in accordance with certain aspects and embodiments herein. As used herein, "bioabsorbable polymer" refers to a polymer or copolymer which is absorbed by the body. "Non-bioabsorbable polymer" refers to a polymer or copolymer which remains in the body without substantial bioerrosion. Both bioabsorbable polymers and non-bioabsorbable polymers for use herein should be "biocompatible" which, as stated above, means that the polymer does not elicit substantially adverse affects when implanted in living tissue.

In one aspect, a monofilament suture is manufactured from a combination of a biocompatible water-soluble glass and a polymer selected from the group consisting of biocompatible bioabsorbable polymer and biocompatible non-bioabsorbable polymer. Useful water-soluble glasses for fabricating monofilament sutures encompass those as described above. As stated above, the water-soluble glass typically includes one or two glass formers, e.g., silicon dioxide, boric oxide and phosphorus pentoxide with one or more glass modifiers, e.g., calcium oxide, sodium oxide, potassium oxide, zinc oxide, barium oxide, magnesium oxide, and mixtures thereof. Preferably, the glass former is phosphorus pentoxide. Preferably the water-soluble glass includes the glass modifiers, sodium oxide and calcium oxide.

The amount of glass former utilized to manufacture glass for a monofilament suture can generally range from about 20 mole percent to about 70 mole percent and more preferably from about 40 mole percent to about 50 mole percent of the total composition. The amount of glass modifier will depend on the specific glass modifier utilized. For example, the glass modifier, sodium oxide, is generally present in an amount of from about 10 mole percent to about 50 mole percent of the total composition. The glass modifier, calcium oxide, is generally present in an amount of from about 5 mole percent to about 40 mole percent of the total composition.

The biocompatible water-soluble glass employed to prepare the monofilament suture includes a therapeutic agent as described above, which can be incorporated into the glass during its manufacture. The amount of therapeutic agent generally ranges from about 0.5 mole percent to about 50 mole percent. Preferably, the therapeutic agent is an antimicrobial agent, and more preferably, the antimicrobial agent is silver, in the form of silver oxide, silver nitrate or silver orthophosphate.

Biocompatible bioabsorbable polymers utilized to manufacture sutures are well known in the art. Suitable biocompatible bioabsorbable polymers include natural polymers such as cat gut and collagen; synthetic bioabsorbable polymers and resins such as those derived from bioabsorbable monomers such as glycolic acid, glycolide, lactic acid, lactide, dioxanone, caprolactone, trimethylene carbonate, etc., and various combinations of these and related polymers. For example, random, block or graft copolymers and blends of the above-mentioned synthetic bioabsorbable polymers are suitable and are intended to be encompassed by the term "bioabsorbable polymer" as used herein.

Biocompatible non-bioabsorbable polymers utilized to manufacture sutures are also well known in the art. Suitable biocompatible non-bioabsorbable polymers include homopolymers and copolymers of polypropylene, polyamides, polyvinyl chlorides, polysulfones, polyurethanes, polytetrafluoroethylene, etc.

Monofilaments containing a combination of biocompatible bioabsorbable polymer or biocompatible non-bioabsorbable polymer and biocompatible water-soluble glass can be conveniently prepared using known techniques for making monofilament sutures as described, e.g., in U.S. Pat. Nos. 5,403,347, 5,217,485, and 5,279,783, each being incorporated herein by reference. In general, the water-soluble glass, preferably in powder or granule form is combined with pellets or powders of the biocompatible bioabsorbable or non-bioabsorbable polymer to form a substantially uniform mixture using conventional techniques known to those skilled in the art and melt extruded to form a filament. Alternatively, using a two-step extrusion process pellets of water-soluble glass and pellets or powder of biocompatible bioabsorbable polymer or biocompatible non-bioabsorbable polymer are combined in a hopper and extruded as a large fiber or rod, which is then added to a second hopper and subsequently extruded to form the monofilament. The water-soluble glass is typically added to the biocompatible bioabsorbable polymer or biocompatible non-bioabsorbable polymer in an amount of from about 0.01 percent by weight to about 10 percent by weight, and preferably from about 0.1 percent by weight to about 5 percent by weight of the biocompatible bioabsorbable or biocompatible non-bioabsorbable polymer. The extruded monofilament is then air dropped and quenched in a water bath to solidify the monofilament. The solidified monofilament may then be drawn and stretched to orient molecules in the suture.

The specific conditions employed for the extruding and stretching operations in manufacturing monofilaments of the therapeutic water-soluble glass and polymer depend on the composition of the polymer resin. For example, a suitable process for the manufacture of monofilaments including bioabsorbable polymers e.g., a glycolide/1,3 dioxane-2-one/1,4 dioxane-2-one copolymer, as described in U.S. Pat. No. 5,403,347, may include the operations of melt extruding polymer resin at a suitable extrusion temperature, e.g., from about 170° C. to about 250° C. to provide a monofilament, stretching the solidified monofilament at a temperature of from about 20° C. to about 90° C. in water (or other suitable liquid medium) or at from about 30° C. to about 100° C. in air (or other suitable gaseous medium) at a stretch ratio of from about 3:1 to about 10:1 to provide a stretched monofilament. A suitable process for the manufacture of monofilaments including polypropylene resin as described in U.S. Pat. No. 5,217,485, may include the operations of melt extruding polymer resin at a suitable extrusion temperature of e.g., from about 190° C. to 230° C., and stretching the solidified filament at a suitable temperature of from about 90° C. to about 180° C. A suitable process for the manufacture of monofilament sutures including polyamide resin as described in U.S. Pat. No. 5,279,783, may include the operations of melt extruding polymer resin containing therapeutic water-soluble glass at a suitable extrusion temperature from about 20° C. to about 50° C. to provide a monofilament, stretching the solidified monofilament at a suitable temperature, e.g., from about 60° C. to about 98° C. in water (or other suitable liquid medium) or from about 100° C. to about 170° C. in air (or other suitable gaseous medium) at a stretch ratio of from about 3.5:1 to about 4.5:1 to provide a stretched monofilament. Optionally, the solidified monofilament may be stretched in air or other suitable gaseous medium preferably at about 30° C. to about 105° C. The suture may then be annealed at a suitable temperature. For example, an annealing temperature of from about 80° C. to about 130° C. may be utilized for a bioabsorbable polymer monofilament suture, about 150° C. for a polypropylene monofilament suture, and from about 20° C. to about 180° C. for a polyamide monofilament suture.

FIG. 1A schematically illustrates a monofilament suture manufacturing operation which is especially suitable for producing larger size sutures, e.g., those of sizes 2/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. A mixture of pellets or powder of biocompatible bioabsorbable polymer and therapeutic water-soluble glass are introduced to the extruder through hopper 12.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact with air currents which might otherwise affect the cooling of the monofilament in an unpredictable manner. In general, barrel zone A of the extruder can be maintained at a temperature of from about 170° C. to 220° C., zone B at from about 180° C. to 230° C. and zone C at from about 190° C. to about 240° C. Additional temperature parameters include: metering pump block 13 at from about 180° C. to about 230° C., spin pack 14 at from about 190° C. to about 230° C., spinneret 15 at from about 180° C. to about 230° C. and quench bath at from about 10° C. to about 80° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament is wrapped around a fist godet 21 provided with nip roll 22 to prevent slippage which might otherwise result from the subsequent stretching operation; and subsequently wrapped around godets 101, 102, 103 and 104 or any other suitable godet arrangement. Monofilament 16 passing from godet 104 is stretched, e.g., with stretch ratios on the order of from about 3:1 to about 10:1 and preferably from about 4:1 to about 7:1, to effect its orientation and thereby increase its tensile strength.

In the stretching operation shown in FIG. 1A, generally suitable for larger size sutures, e.g., sizes 2, to 3/0, monofilament 16 is drawn through hot water (or other suitable liquid medium) draw bath 23 by means of godets 24, 105, 106, 107 and 108 or any other suitable arrangement of godets which rotate at a higher-speed than godet 104 to provide the desired stretch ratio. The temperature of hot water draw bath 23 is advantageously from about 30° C. to about 50° C.

Figure 1B:
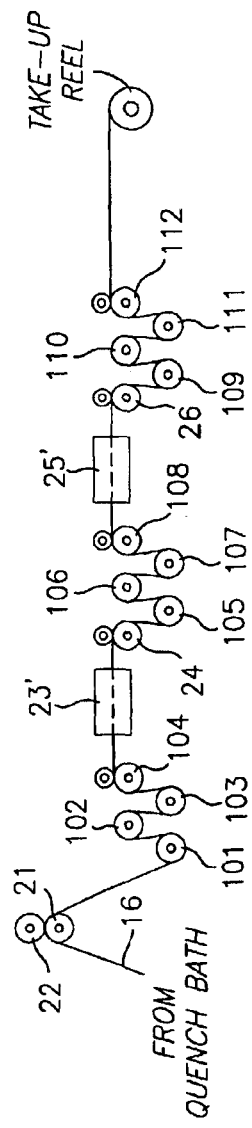
FIG. 1B is a modification of the apparatus of FIG. 1A which is particularly suitable for manufacturing the monofilament sutures of smaller size, e.g., sizes 4/0 and smaller.

In the alternative stretching operation shown in FIG. 1B, generally preferred from smaller sutures sizes, e.g., sizes 3/0 to 8/0, monofilament 16 is drawn by godets 24, 105, 106, 107 and 108 or any other suitable godet arrangement through hot air convection oven chamber 23' at a temperature of from about 30° C. to about 80° C. and preferably from about 30° C. to about 60° C. to provide the desired amount of stretch. Following the stretching operation shown in FIG. 1A or 1B, monofilament 16 optionally may be subjected to an on-line annealing and/or additional stretching without shrinkage or relaxation with shrinkage operation as a result of which the monofilament shrinks. In the processes of FIGS. 1A and 1B, on line annealing with or without relaxation when desired is accomplished by driving monofilament 16 by godets 26, 109, 110, 111, and 112 or any other suitable godet arrangement through second hot air oven chamber 25 at a temperature of from about 30° C. to about 120° C. and preferably from about 30° C. to about 60° C. During the relaxation process, at these temperatures, monofilament 16 will generally recover to within about 80 to about 97 percent, and preferably to within about 95 percent, of its pre-annealed length to provide the finished suture. For relaxation, the third godet rotates at a slower speed than the second godet thus relieving tension of the filament.

Annealing of the suture also may be accomplished without shrinkage of the suture. In carrying out the annealing operation, the desired length of suture may be wound around a spool or rack and the spool or rack placed in a heating cabinet maintained at the desired temperature as described above. After a suitable period of residency in the heating cabinet, e.g., about 18 hours or so, the suture will have undergone essentially no shrinkage. As shown in U.S. Pat. No. 3,630,205, the spool or rack may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

Figure 2:
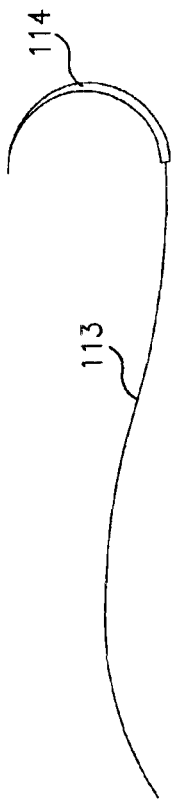
FIG. 2 is a perspective view of a suture attached to a needle.

The suture 113, may be attached to a surgical needle 114 as shown in FIG. 2 by methods well known in the art. Wounds may be sutured by passing the needled suture through tissue to create would closure. The needle preferably is then removed from the suture and the suture tied.

In another aspect, multifilament sutures provided which include filaments fabricated from a biocompatible water-soluble glass with or without a therapeutic agent. Useful biocompatible water-soluble glasses are described above. The water-soluble glass is preferably in the form of fine particles or coarse granules. The water-soluble glass optionally includes a therapeutic agent, e.g., silver, in an amount ranging from about 1 mole percent to about 50 mole percent of glass. Multifilament sutures herein can include water-soluble glass filaments commingled with filaments fabricated from a polymer selected from the group consisting of biocompatible bioabsorbable polymer or biocompatible non-bioabsorbable polymer or filaments fabricated from a combination of biocompatible water-soluble glass and a polymer selected form the group consisting of biocompatible bioabsorbable polymer and biocompatible non-bioabsorbable polymer. Suitable biocompatible bioabsorbable polymers and biocompatible non-bioabsorbable polymers are typically the same as those utilized to prepare a monofilament suture. Multifilament sutures in accordance with this disclosure may be prepared by methods known in the art. See, e.g., U.S. Pat. Nos. 5,019,093, 5,059,213 and 5,423,851, each being incorporated herein by reference.

Examples of multifilament sutures are spun and braided sutures. Typically, braided sutures comprise multifilament yarns, denominated "sheath yarns", each sheath yarn being made up of individual filaments with the sheath yarns interlacing in a regular crisscross pattern. Optionally, a core component may be included. The core may be a cabled structure made up of plied yarns each of which has been given a twist in one direction, the plied yarns then being combined to form a core which is then given a twist in a second, opposite direction. The core may be a spun or zero twist yarn consisting of filaments which are essentially parallel to each other and which are held in contiguity by a treating fluid, e.g., spin finish, which includes lubricants and other agents to facilitate processing of the yarn.

Certain defining characteristics of a braided suture useful herein include the following:

(1) overall suture denier;
(2) the pattern of the interlocking yarns expressed as the pick count, which is to say, the number of crossovers of individual sheath yarns per linear inch of suture;
(3) the number of sheath yarns comprising the braid;
(4) the denier of the individual filaments comprising each sheath yarn; and
(5) the denier of the core, where present.

In one example, the overall denier of the braided suture can vary from about 50 to about 4000. Within this range, the ranges of overall denier for particular sutures may be from about 50 to about 125 denier; from about 125 to about 200 denier; from above about 200 to about 300 denier; from above 300 to about 500 denier; from above about 500 to about 800 denier; from above about 800 to about 1500 denier; from above about 1500 to about 2000 denier; and, from above about 200 to about 3600 denier. For a suture of any range of overall denier, pick count can vary from about 35 to about 100 crossovers/inch with about 40–85 crossovers/inch being preferred. The term "pick count" refers to the number of crossovers of sheath yarns per linear inch of suture and, together with the overall denier of the suture, the denier of the individual filaments constituting a sheath yarn and the number of sheath yarns employed, defines the principal construction characteristics of the braided suture herein. For a suture of a particular range of denier and number of sheath yarns, pick count is advantageously established to achieve a balance in the properties desired. In general, with increasing pick count, surface roughness of the suture tends to increase and with decreasing pick count, the ability of the external braid sheath to contain the core (if present) tends to decrease even reaching the point where the braid may become so loose as to result in the core protruding therethrough. In one embodiment, a low pick count may be utilized to achieve optimum surface smoothness, consistent, of course, with the need to provide a compact braid which prevents the core (if present) from protruding through the exterior sheath yarn structure. The number of sheath yarns bears some relation to overall suture denier, the number generally increasing with the weight of the suture. Thus, across the range of suture weight (denier) indicated above, a braided suture can be constructed with from, e.g., about 3 up to as many as about 36 individual sheath yarns constructed from individual filaments having varying deniers. For example, deniers of individual filaments may vary from about 0.2 to about 6.0 for the broad range. Pick counts vary from about 40 to about 85 and the deniers of individual filaments vary from about 0.8 to about 3.0, and advantageously from about 0.8 to about 2.0. The number of such filaments present in a particular sheath yarn will depend on the overall denier of the suture as well as the number of sheath yarns utilized in the construction of the suture. For all but the lowest range of overall denier, a braided suture herein can optionally be constructed around a filamentous core which itself can be braided or which can be provided in some other configuration such as a twist, ply, cable, etc. The filament(s) comprising the core need not be as fine as those comprising the sheath yarns. It is particularly advantageous for sutures of heavier denier to possess a core.

Combinations of water-soluble glass, therapeutic water-soluble glass, biocompatible absorbable polymer and biocompatible non-absorbable polymer may be fabricated by commingling individual filaments of each respective material as desired to form a yarn. The percent of absorbable water-soluble glass or therapeutic water-soluble glass can range from 0–100% of a multifilament suture. When glass is less than 100% of the total filament content, the balance of commingled filaments can be any percentage combination of biocompatible bioabsorbable polymer filaments and biocompatible non-bioabsorbable polymer filaments.

When constructing a multifilament suture herein, individual filaments are first provided and then they are combined to form a yarn. Individual filaments are optionally prepared by extrusion from a glass or polymer melt. Extrusion processes are well-known in the art. For example, spun filaments may be extruded through a spinneret and quenched in a chamber. The number of filaments present in the yarn will depend on the overall denier of the suture and whether the yarn is to be incorporated into a sheath or core.

After the spun filaments are quenched, a spin finish applicator can apply a spin finish to the filaments which are then passed around lube godet. During this procedure, the filaments combine in parallel contiguous arrangement to form yarn. Yarn is then passed around a series of. godets for drawing and relaxing the suture yarn. The yarn speed can be from about 200 to about 1500 meters per minute, preferably about 900 to about 1300 meters per minute, and more preferably about 1000 to about 1200 meters per minute. The yarn is under a tension of from about 3 to about 10 grams, preferably about 3 to about 9 grams, and more preferably from about 4 to about 8 grams.

In one embodiment exemplified in U.S. Pat. No. 5,423,859, incorporated herein by reference, the yarn is subject to jet entanglement. In jet entanglement a fluid, preferably air or some other gas, is forced at elevated pressure into a chamber through which a multifilament yarn is passed. The turbulence of the jet causes the filaments to entangle or intermingle in the area impinged by the jet. The movement of the yarn and the size and shape of the chamber can interact to cause pulsations in the turbulence. Thus, even with a constant pressure air supply, the yarn can exit the chamber with discrete regularly spaced apart areas of entanglement alternating with non-entangled areas. The entangled portions are retained by the yarn through subsequent processing steps. Jet entanglement can accomplish many of the features of twisting.

In another aspect, a coating composition for a surgical device, e.g., a suture, pledget, etc., is provided. The coating composition includes a biocompatible non-bioabsorbable polymer or biocompatible bioabsorbable polymer, and a water-soluble glass wherein the coating composition is adapted to coat the surgical device. Indeed, in accordance with the present disclosure, therapeutic water-soluble glass can be added to conventional suture coating compositions to provide a therapeutically active sustained release modality at any suture site. Particularly useful coating compositions are described in U.S. Pat. Nos. 5,312,437, 5,425,949, 5,939,191, 5,716,376 and 5,123,912, each being incorporated herein by reference.

U.S. Pat. No. 5,312,437 (the "437 patent") describes, inter alia, an absorbable coating composition including the product obtained by reacting a mixture of poly(oxypropylene) glycol and a lactide/glycolide copolymer in the presence or absence of an initiator. An effective amount of therapeutic water-soluble glass is combined into a solution or dispersion of the '437 patent reaction product to form a suspension for application to sutures. U.S. Pat. No. 5,425,949 (the "949 patent") describes, inter alia, a coating composition including a bioabsorbable copolymer which is obtained by polymerizing a major amount of epsilon-caprolactone and a minor amount of at least one other copolymerizable monomer in the presence of an initiator possessing at least two carboxylic acid groups. An effective amount of therapeutic water-soluble glass is combined into a solution or dispersion of the '949 patent bioabsorbable copolymer to form a suspension for application to sutures. U.S. Pat. No. 5,939,191 (the "191 patent") describes, inter alia, a bioabsorbable copolymer employed as a coating composition. The bioabsorbable copolymer is obtained by polymerizing a major amount of epsilon-caprolactone and a minor amount of at least one other copolymerizable monomer or mixture of such monomers in the presence of a polyhydric alcohol initiator. An effective amount of therapeutic water-soluble glass is combined into a solution or dispersion of the '191 patent bioabsorbable copolymer to form a suspension for application to sutures. U.S. Pat. No. 5,13,912 (the "912 patent") describes, inter alia, an absorbable polymeric coating composition including either (i) a copolymer derived from the copolymerization of a low molecular weight polyalkylene glycol, a glycolide monomer and a lactide monomer or (ii) a copolymer derived from the copolymerization of a low molecular weight polyalkylene glycol and a preformed copolymer of lactide and glycolide. An effective amount of therapeutic water-soluble glass is combined into a solution or dispersion of the '912 patent copolymer to form a suspension for application to sutures. The above solutions or dispersions may be formulated by any technique known to those skilled in the art. For example, the products and copolymers described above may be dissolved in a suitable solvent such as methylene chloride or dispersed using suspending agents or emulsifiers. The therapeutic water-soluble glass is combined into solution or suspension by conventional techniques including stirring, agitation and homogenization.

In one suture coating embodiment herein, a biocompatible bioabsorbable polymer includes a mixture of a copolymer containing caprolactone with an ester of fatty acid as described, e.g., in U.S. Pat. No. 5,716,376. Preferably, such a mixture includes an ester of a fatty acid as a predominant component. A "predominant component" is a component which is present in an amount greater than about 50 weight percent. A "minor component" is a component which is present in an amount up to about 50 weight percent. The minor component includes copolymers containing caprolactone.

Suitable caprolactone-containing copolymers include copolymers which may be synthesized by well known conventional polymerization techniques; see e.g., Principles of Polymerization, George Odian, III Edition; 1991, pp. 569–573, incorporated herein by reference.

Preferably, the caprolactone-containing copolymer is obtained by polymerizing a major amount of epsilon-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

The copolymer herein can contain from about 70 to about 98, and preferably from about 80 to about 95, weight percent epsilon-caprolactone derived units, the balance of the copolymer being derived from other copolymerizable monomer(s).

Suitable monomers which can be copolymerized with epsilon-caprolactone include alkylene carbonates such as trimethylene carbonate, tetramethylene carbonate, dimethyl trimethylene carbonate; dioxanones; dioxepanones; absorbable cyclic amides; absorbable cyclic ether-esters derived from crown ethers; hydroxy acids capable of esterification, including both alpha hydroxy acids (such as glycolic acid and lactic acid) and beta hydroxy acids (such as beta hydroxybutyric acid and gamma hydroxyvaleric acid); polyalkyl ethers (such as polyethylene glycol and polypropylene glycol) and combinations thereof; with glycolide being a preferred monomer.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N,',N'-tetrakis (2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being preferred.

The polyhydric alcohol initiator is generally employed in small amounts, e.g., from about 0.01 to about 5, and preferably from about 0.1 to about 3, weight percent of the total monomer mixture.

Suitable esters of fatty acids include esters of the formula:

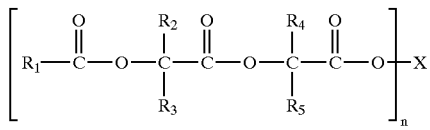

wherein x is an alkaline-earth metal or ion thereof and $R_1$ is $C_{10}$ or greater alkyl, $R_2$ is H, or $C_1$–$C_3$ alkyl, $R_3$ is H, or $C_1$–$C_3$ alkyl, $R_4$ is H, or $C_1$–$C_3$ alkyl, $R_5$ is H, or $C_1$–$C_3$ alkyl, and n>1. Such suitable fatty acids include calcium, magnesium, aluminum, barium, or zinc stearoyl lactylate; calcium, magnesium, aluminum, barium, or zinc palmityl lactylate; calcium, magnesium, aluminum, barium, or zinc olelyl lactylate; with calcium stearoly-2-lactylate (such as the calcium stearoyl-2-lactylate commercially available under the trademark VERV from American Ingredients Co., Kansas City, Mo.) being preferred.

The caprolactone-containing copolymer and the fatty acid ester are non-toxic; a mixture of the two is non-toxic as well. The caprolactone-containing copolymer/fatty acid mixture constitutes a biocompatible bioabsorbable polymer herein suitable for combination with therapeutic absorbable glass to form a coating suspension for application to sutures.

Biocompatible non-absorbable polymers useful in the coating composition include, but are not limited to, silicon polymers, waxes and combinations thereof. The silicon polymers can further include a cross-linking agent, e.g., PERKADOX®, available from Akzo Nobel, that polymerizes when heated.

The water-soluble glass of the coating composition typically includes one or two glass former, e.g., silicon dioxide, boric oxide and phosphorus pentoxide with one or more glass modifiers, e.g., calcium oxide, sodium oxide, potassium oxide, zinc oxide, barium oxide, magnesium oxide, and mixtures thereof Preferably, the water-soluble glass includes phosphorus pentoxide as the glass former, and can further include sodium oxide and calcium oxide as glass modifiers. The amount of glass former typically ranges from about 20 mole percent to about 70 mole percent, and more preferably from about 40 mole percent to about 50 mole percent of the total composition of water-soluble glass. The amount of glass modifier will depend on the specific glass modifier utilized. For example, sodium oxide is generally present in an amount of from about 10 mole percent to about 50 mole percent of the water-soluble glass, whereas calcium oxide is generally present in an amount of from about 5 mole percent to about 40 mole percent of the water-soluble glass.

In one particularly useful embodiment, the water-soluble glass includes from about 40 mole percent to about 50 mole percent phosphorus pentoxide, from about 20 mole percent to about 40 mole percent sodium oxide, and from about 10 mole percent to about 30 mole percent calcium oxide (see Example 1).

The therapeutic agent incorporated into the glass utilized for the coating compositions is preferably a metal as described above. Most preferably, the metal is silver, in the form of silver oxide, silver nitrate or silver orthophosphate. The amount of therapeutic agent, e.g., silver, incorporated into the glass is generally from about 0.1 to about 10 mole percent, and preferably from about 1 to about 5 mole percent.

The water-soluble glass utilized in the foregoing coating compositions can be formed by conventional methods. For example, as described above, the glass can be formed by mixing the components, i.e., glass formers, glass modifiers, and therapeutic agents, e.g., silver compounds, and heating the mixture to about 1000 to about 1200° C., and preferably about 1100° C., to form a glass. Following glass formation, the glass is pulverized into a fine powder or coarse granules by milling. Typically, the glass particle size ranges from about 1 to about 100 microns, and preferably from about 5 to about 20 microns. Water-soluble glasses are also commercially available, e.g., ARGLAES® glass (Giltech Limited, Great Britain).

In general, the coating compositions for surgical devices can be prepared by dispersing the water-soluble glass in the biocompatible bioabsorbable polymer or biocompatible non-absorbable polymer described above using any conventional technique known to one skilled in the art. For example, the glass in powder or granule form can be combined with the bioabsorbable or non-bioabsorbable polymer and thoroughly mixed using a homogenizer. It is contemplated that the glass and absorbable polymer can be mixed together in powder or pellet form and then suspended using suitable solvents or suspending agents. Suitable solvents for silicon based coatings include xylene. The coating composition typically contains from about 10 to about 75 percent by weight of the water-soluble glass, and preferably from about 25 to about 50 percent by weight of the water-soluble glass. In the case where the non-bioabsorbable polymer is a silicon polymer including a cross-linking agent, the mixture is then heated to polymerize the coating on the surgical device and to evaporate solvent present in the coating. Prior to and/or during its application onto the surgical device, the coating composition can be agitated to ensure that the glass is uniformly distributed throughout the composition.

In another aspect, sutures having therapeutic activity are prepared by coating the sutures with a coating composition as described. Such a coating composition includes a therapeutic water-soluble glass which includes a therapeutically effective amount of a therapeutic agent. A therapeutically effective amount of a therapeutic agent is that amount required to aid or promote wound repair, e.g., to minimize bacterial growth on and in the suture, and will depend on the type of body tissue and the nature and extent of tissue injury. The therapeutically effective amount can be determined readily by one skilled in the art. The coating composition can further include a biocompatible bioabsorbable polymer or biocompatible non-bioabsorbable polymer as described above. The coating compositions can be applied to any type of monofilament or multifilament surgical suture including the monofilament sutures fabricated from water-soluble glass and biocompatible bioabsorbable or non-bioabsorbable polymer, and multifilament sutures including water-soluble glass as described above. Preferably, coating compositions prepared from biocompatible bioabsorbable polymers are applied to sutures fabricated from biocompatible bioabsorbable polymers, and coating compositions prepared with biocompatible non-bioabsorbable polymers are applied to sutures fabricated from biocompatible non-bioabsorbable polymers.

In a particularly useful embodiment, a bioabsorbable multifilament suture, e.g., POLYSORB® or DEXON®, is coated with a coating composition fabricated from therapeutic water-soluble glass and a biocompatible bioabsorbable polymer which includes a mixture of caprolactone-containing polymers and fatty acid esters as described above. In a particularly preferred embodiment, a braided suture, described, e.g., in U.S. Pat. Nos. 5,019,093, or 5,059,213 is coated with a coating composition which includes a mixture of therapeutic water-soluble glass and caprolactone-containing polymers and fatty acid esters as described above.

Another particularly useful embodiment provides a monofilament suture or multifilament suture made of polyethylene, nylon, or polyester, coated with a non-bioabsorbable coating prepared from a silicon polymer in combination with therapeutic water-soluble glass, and more preferably a polyester braided suture, e.g., TICRON®, or a nylon braided suture, e.g., BRALON® (United States Surgical), coated with a silicon polymer and therapeutic water-soluble glass.

The coating composition is applied to the suture by any conventional technique known in the art. Suitable techniques useful for applying the coating to the suture include, but are not limited to, dipping, spraying, wiping and brushing. Where the substrate is in the form of a braided suture, techniques used for applying a coating or other treatment to a fiber may be employed to contact the substrate. Once the suture has contacted the coating composition, heat is used to evaporate the solvent.

The amount of coating composition applied to a suture will vary depending upon the structure of the suture, e.g., the number of filaments, tightness of braid or twist, the size of the suture and its composition. Suitable coating levels range from about 0.3 percent by weight to about 10 percent by weight and preferably from about 0.5 percent by weight to about 5 percent by weight, based on the total weight of the suture and the applied coating composition. For example, the amount of coating composition applied to a polyester braided suture, e.g., TICRON®, generally ranges form about 0.5 percent by weight to about 3.0 percent by weight, based on the total weight of the suture and the applied coating composition. The amount of coating composition applied to a POLYSORB® suture may generally range from about 0.82 percent by weight to about 5.0 percent by weight, based on the total weight of the suture and the applied coating composition. Once the suture is coated, it can be sterilized by any technique known to one skilled in the art, e.g., by exposure to gaseous ethylene oxide.

The coated suture may be attached to a surgical needle by methods well known in the art. Wounds may be sutured by passing the needled suture through tissue to create wound closure. The needle preferably is then removed from the suture through tissue to create wound closure. The needle preferably is then removed from the suture and the suture tied. The coating advantageously enhances the surgeon's ability to pass the suture through tissue as well as to increase the ease and security with which he/she can tie the suture. Further, the coating on the suture provides sustained release of a therapeutic agent over a desirable period of time at a desired locus.

Figure 3:
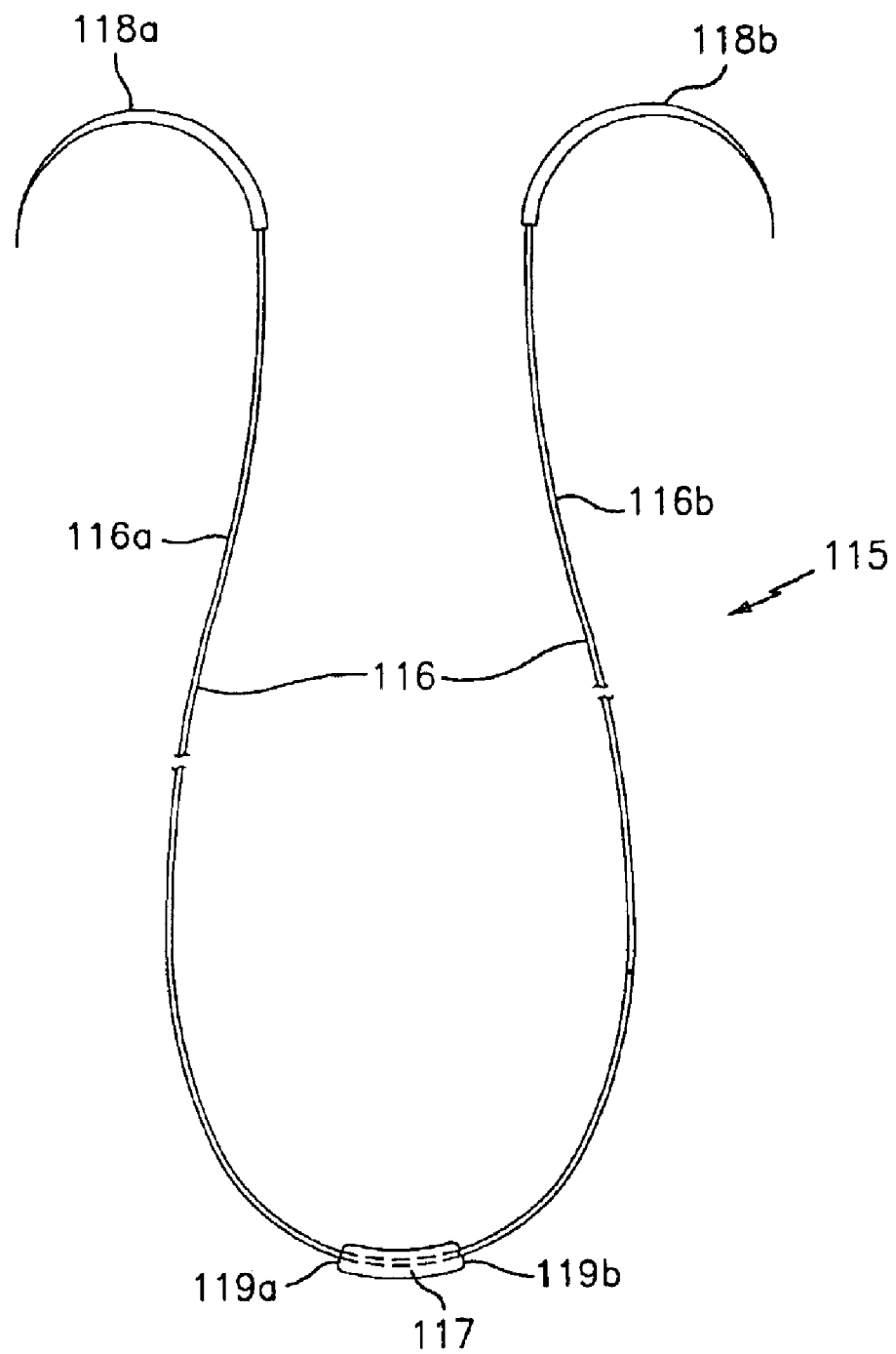
FIG. 3 is a perspective view of a needled suture with attached pledget.

In another aspect, pledgets having therapeutic activity are provided wherein therapeutic water-soluble glass is incorporated in the pledget. In one embodiment, the water-soluble glass is a coating on the pledget. In one embodiment, the water-soluble glass is contained within the interstices of the pledget In another embodiment, the water-soluble glass is coated onto the pledget and also contained within the interstices of the pledget. In another embodiment, the pledget is coated with a coating composition, the coating composition including a therapeutic water-soluble glass. Pledgets are well known in the art. A pledget is a compress or cushioning pad that can be laid over a wound or into a cavity to apply medication, exclude air, retain dressings or absorb matter discharged. Typically, a pledget is used with a suture in various surgical processes involving closing of wounds of living tissue to buttress the tissue and inhibit the suture from cutting into the tissue. FIG. 3 illustrates a needled-suture with an attached pledget.

The surgical device, generally denoted by numeral 115, has suture 116, and a pledget 117 attached to a central region of suture 116. For most applications, the suture is double-armed, including needles 118a and 118b attached to each end of suture 116. Suture/pledget junctions 119a and 119b illustrate where suture 116 passes through pledget 117 with the portion of suture 116 shown in phantom disposed behind pledget 117 in order to accomplish the purpose and objective of the suture pledget combination. Suture portions 116a and 116b extend from the pledget to needles 118a and 118b, respectively. The surgical device can also include a thickening agent made of e.g., collagen, gelatin, etc., disposed on at least a portion of the suture adjacent to the pledget. The thickened agent acts to buttress a portion of the suture adjacent to the pledget to eliminate the tendency of the suture to become tangled or twisted about the pledget.

Pledgets can be any shape, e.g., rectangular, circular, ellipsoidal or polygonal, and are typically fabricated from a non-woven fabric including fibers of a biocompatible bioabsorbable polymer or a biocompatible non-bioabsorbable polymer.

Suitable biocompatible bioabsorbable pledget polymers include, but are not limited to, homopolymers and copolymers of polyglycolic acid, glycolide, lactide, lactic acid, dioxanone, epsilon-caprolactone, trimethylene carbonate and mixtures thereof. Examples of biocompatible non-bioabsorbable pledget polymers include polyesters, polyurethane and polytetrafluoroethylene. A particularly preferred biocompatible non-bioabsorbable pledget consists of polytetrafluoroethylene fibers. Examples of various methods of manufacturing these polymers and, in some instances, pledgets made thereof, may be found in U.S. Pat. Nos.

2,929,800; 3,929,804; 3,428,711; 3,557,044; 4,034,850; 4,043,331; 4,044,404; 4,127,124; 4,164,046; 4,549,545; and 5,393,594, each being incorporated herein by reference.

In a particularly useful embodiment, the pledget is made from a low density biocompatible bioabsorbable non-woven fabric which includes fibers of glycolide and lactide as described, e.g., in foregoing U.S. Pat. No. 5,393,594.

In an alternative embodiment, the bioabsorbable non-woven fabric can be manufactured from an 18/82 (mole percent) glycolide/lactide polymer yarn. Filaments for this embodiment can be manufactured in accordance with methods disclosed in U.S. Pat. No. 5,232,648, the contents of which are incorporated herein by reference.

The water-soluble glass and therapeutic agent utilized in coating compositions for pledgets are the same as those utilized in the foregoing coating compositions to coat sutures. Preferably, the water-soluble glass includes phosphorus pentoxide as the glass former, and can further include sodium oxide and calcium oxide as the glass modifiers. The amount of phosphorus pentoxide typically ranges from about 20 mole percent to about 70 mole percent of the water-soluble glass. Sodium oxide is generally present in an amount of from about 10 mole percent to about 50 mole percent of the water-soluble glass, whereas calcium oxide is generally present in an amount of from about 5 mole percent to about 40 mole percent of the water-soluble glass.

In a particularly useful embodiment, the water-soluble glass includes from about 40 mole percent to about 50 mole percent phosphorus pentoxide, from about 20 mole percent to about 40 mole percent sodium oxide, and from about 10 mole percent to about 30 mole percent calcium oxide (see Example 1).

Preferably, the therapeutic agent incorporated into the glass utilized for the coating composition of the pledget is a metal as described above. Most preferably, the metal is a silver in the form of silver oxide, silver nitrate or silver orthophosphate. The amount of therapeutic agent, e.g., silver, incorporated into the glass is generally from about 0.5 to about 10 mole percent, and preferably from about 1 to about 5 percent. A therapeutically effective amount of a therapeutic agent is that amount required to aid or promote wound repair, e.g., to minimize bacterial growth in, on or near the pledget, and will depend on the type of body tissue and the nature and extent of tissue injury. The coating composition can further include a biocompatible bioabsorbable polymer or biocompatible non-bioabsorbable polymer as described above. Preferably, coating compositions prepared from biocompatible bioabsorbable polymers are applied to pledgets manufactured from bioabsorbable polymers, and coating compositions prepared with biocompatible non-bioabsorbable polymers are applied to pledgets fabricated from biocompatible non-bioabsorbable polymers.

In a particularly useful embodiment, a pledget fabricated with glycolide and lactide as described in foregoing U.S. Pat. No. 5,393,594 is coated with a coating composition made from therapeutic water-soluble glass and a biocompatible bioabsorbable polymer which includes a mixture of caprolactone-containing polymers and fatty acid esters as described above.

In general, the coating compositions utilized to coat pledgets can be prepared by dispersing the water-soluble glass in powder or granule form in any nonpolar or polar solvent using a homogenizer. For example, a suitable solvent mixture for dispersing the water-soluble glass can include methylene chloride, hexanes, and/or ethanol. It is contemplated that the biocompatible bioabsorbable polymer or biocompatible non-bioabsorbable polymer in powder or granule form can be mixed with the water-soluble glass and then dispersed in the foregoing solvents. Alternatively, the biocompatible bioabsorbable polymer or biocompatible non-bioabsorbable polymer can be prepared and dispersed or dissolved in a solvent as described above, followed by the addition of water-soluble glass in powder or granule form, or the glass may be applied to the pledget using solvent or solvents with no polymer. For example, the water-soluble glass can also be contained within the interstices of the pledget by dipping the pledget in a slurry of water-soluble glass and solvents as described above and removing the solvent from the pledget, e.g., by evaporation.

The coating composition can be applied to the pledget in any number of ways. Suitable techniques for applying the coating composition to the pledget or pledget and suture include, but are not limited to dipping, spraying, wiping and brushing, with dipping being preferred. The amount of coating composition applied to the pledget will vary depending on the structure, size and composition of the pledget. Typically, the amount of coating composition applied to the pledget ranges from 0.3 percent by weight to about 10 percent by weight, based on the total weight of the pledget and the applied coating composition. Prior to and/or during its application on the pledget, the coating composition can be agitated to ensure that the glass alone or glass combined with polymer is uniformly distributed throughout the composition.

The following examples are included for purposes of illustrating certain embodiments and are not intended to limit the scope of the present disclosure.

EXAMPLE 1

Preparation of Water-Soluble Glass Utilized in Coating Composition

Water-soluble glass is prepared using the components listed in Table I below.

TABLE I

| | |
|---|---|
| $Na_2$ | 20–40 mole % |
| CaO | 10–30 mole % |
| $Ag_2O$ | 0–10 mole % |
| $P_2O_5$ | 40–50 mole % |

The components are mixed until homogeneous in a drum mixture. Mixed constituents are weighted in crucibles and heated to about 1100° C. at which temperature they from a glass. When the reaction is complete, the weight is measured again. The actual weight loss is compared with the calculated stiochiometric weight loss. If the difference is within 1.5% of the batch mass, Atomic Absorption Spectrophotometer techniques are used to determine sodium and calcium concentration. The composition is corrected or rejected as appropriate. The glass is poured onto polished steel sheets and cooled. The cullet is reduced to the desired particle by milling. Particle size analysis is done using a Coulter Counter. Sample rods are cast from powder and annealed.

EXAMPLE 2

Preparation of Bioabsorbable Polymer Utilized in Coating Composition

A. Preparation of 10/90 Epsilon-caprolactone/glycolide Star Copolymer Component of the Bioabsorbable Polymer The epsilon-caprolactone/glycolide copolymer component was prepared using the components listed in Table II below.

TABLE II

| Glycolide (grams) | Initiator MANNITOL (grams) | Epsilon-Caprolactone (grams) | Catalyst (Stannous Octoate) (grams) |
|---|---|---|---|
| 2,000 | 30.0 | 18,000 | 2.0–5.0 (4.0) |
| 4,000 | 60.0 | 36,000 | 6.0–10.0 (8.0) |

The monomers, glycolide and epsilon-caprolactone, and initiator, d-mannitol, were added to a reactor and mixed under nitrogen for approximately 6 hours. Subsequently, the reactor was heated to a polymerization temperature of 160° C. The catalyst, stannous octoate was then added and the mixture was polymerized at 160° C. under pressure for 16 hours. The resulting polymer was extruded using an extruder and pelletizer, and then dried under vacuum to remove water.

B. Preparation of Complete Bioabsorbable Polymer

The bioabsorbable polymer coating for various sizes of braided sutures was prepared using the components listed in Table III below.

TABLE III

| Size of Suture | Epsilon-Caprolaconte/glycolide copolymer (grams) | Calcium Stearoyl/lactylate (grams) | Methylene Chloride (grams) | Ethanol (grams) | Hexanes (grams) |
|---|---|---|---|---|---|
| 2–3/0 | 53.0 ± .1 | 57.5 ± 0.1 | 1624 ± 1.0 | 287 ± 1.0 | 189 ± 1.0 |
| 4/0–6/0 | 46.1 ± 0.1 | 49.9 ± 0.1 | 1624 ± 1.0 | 287 ± 1.0 | 189 ± 1.0 |
| 7/0–8/0 | 18.2 ± 0.1 | 19.8 ± 0.1 | 812 ± 1.0 | 143 ± 1.0 | 95 ± 1.0 |

Methylene chloride, ethanol, calcium stearoyl lactylate and epsilon-caprolactone/glycolide (prepared as described in Example 2A) were added to a container and the suspension was stirred at room temperature for approximately 60 minutes. Hexanes were then added to the suspension which was then stirred for a minimum of 2 hours.

EXAMPLE 3

Preparation of Complete Coating Composition 80.0 Grams of the resulting bioabsorbable polymer coating prepared as described in Example 2 were mixed with 0.25 grams to 4.0 grams-of water-soluble glass prepared as described in Example 1 to form the coating composition.

It will be understood that various modifications may be made to the embodiments disclosed herein. Therefore, the above description should not be construed as limiting, but merely as exemplifications of the preferred embodiments. Those skilled in the art will envision other modifications within the scope and spirit of the claims appended hereto.

What is claimed is:

1. A coating composition for a surgical device comprising: therapeutic water-soluble glass and a biocompatible polymer selected from the group consisting of bioabsorbable polymers and non-bioabsorbable polymers, wherein the coating composition is adapted to coat the surgical device.

2. A coating composition according to claim 1 wherein the therapeutic water-soluble glass contains a therapeutic agent selected from the group consisting of antimicrobial agent, growth factor, anti-inflammatory agent, analgesic, immunosuppressant and combinations thereof.

3. A coating composition according to claim 2 wherein the antimicrobial agent is a metal compound selected from the group consisting of copper, silver, zinc, magnesium, cerium, manganese, bismuth, selenium, boron and combinations thereof.

4. A coating composition according to claim 2 wherein the antimicrobial agent is a silver compound.

5. A coating composition according to claim 4 wherein the silver compound is selected from the group consisting of silver oxide, silver nitrate and silver orthophosphate.

6. A coating composition according to claim 1 wherein the biocompatible polymer is a bioabsorbable polymer comprising:
   a) a copolymer including a predominant amount of epsilon-caprolactone and a minor amount of at least one other copolymerizable monomer; and
   b) a salt of a lactylate ester of a $C_{10}$ or greater fatty acid selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, zinc palmityl lactylate, calcium olelyl lactylate, magnesium olelyl lactylate, aluminum olelyl lactylate, barium olelyl lactylate, calcium stearoyl lactylate and zinc olelyl lactylate.

7. A coating composition according to claim 6 wherein the salt of the lactylate ester is calcium stearoyl lactylate.

8. A coating composition according to claim 6 wherein the coating includes from about 5 to about 95 percent by weight of the copolymer component, the remainder being the salt of a lactylate ester of a $C_{10}$ or greater fatty acid.

9. A coating composition according to claim 1 wherein the water-soluble glass includes phosphorus pentoxide as a glass former.

10. A coating composition according to claim 9 wherein the water-soluble glass further includes sodium oxide and calcium oxide.

11. A coating composition according to claim 1 wherein the polymer is a non-bioabsorbable polymer selected from the group consisting of silicon polymers, waxes and combinations thereof.

12. A coating composition according to claim 11 wherein the non-bioabsorbable polymer is a silicon polymer.

13. A coating composition according to claim 12 wherein the silicon polymer includes a crosslinking agent.

14. A coating composition according to claim 6 wherein the water-soluble glass includes phosphorus pentoxide, sodium oxide, calcium oxide and silver.

15. A coating composition according to claim 12 wherein the water-soluble glass includes phosphorous pentoxide, sodium oxide, calcium oxide and silver.

16. A coating composition according to claim 1 wherein the coating composition further includes a solvent.

17. A suture coated with a coating composition, the coating composition comprising therapeutic water-soluble glass and a biocompatible polymer selected from the group consisting of bioabsorbable polymers and non-bioabsorbable polymers.

18. A suture coated with a coating composition according to claim 17 wherein the therapeutic water-soluble glass contains an antimicrobial agent.

19. A coating composition according to claim 18 wherein the antimicrobial agent is silver.

20. A suture coated with a coating composition according to claim 17 wherein the biocompatible polymer is a bioabsorbable polymer comprising:
a) a copolymer including a predominant amount of epsilon-caprolactone and a minor amount of at least one other copolymerizable monomer; and
b) a salt of a lactylate ester of a $C_{10}$ or greater fatty acid selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate or zinc palmityl lactylate, calcium olelyl lactylate, magnesium olelyl lactylate, aluminum olelyl lactylate, barium olelyl lactylate, calcium stearoyl lactylate and zinc lactylate.

21. A suture coated with a coating composition according to claim 17 wherein the suture is a multifilament suture.

22. A suture coated with a coating composition according to claim 21 wherein the multifilament suture is a braided suture.

23. A suture coated with a coating composition according to claim 17 wherein the suture is a monofilament suture.

24. A suture coated with a coating composition according to claim 17 wherein the suture includes a material selected from the group consisting of bioabsorbable polymer, nylon, linen, silk, cotton, polyester, polypropylene and polyethylene.

25. A suture coated with a coating composition according to claim 24 wherein the bioabsorbable polymer is derived from bioabsorbable monomers selected from the group consisting of glycolic acid, glycolide, lactic acid, lactide, dioxanone, trimethylene carbonate and combinations thereof.

26. A monofilament suture comprising therapeutic water-soluble glass and a polymer selected from the group consisting of biocompatible bioabsorbable polymer and biocompatible non-bioabsorbable polymer.

27. A monofilament suture according to claim 26 wherein the therapeutic water-soluble glass includes phosphorus pentoxide.

28. A monofilament suture according to claim 27 wherein the therapeutic water-soluble glass further includes sodium oxide and calcium oxide.

29. A monofilament suture according to claim 26 wherein the therapeutic water-soluble glass contains at least one antimicrobial agent.

30. A monofilament suture according to claim 29 wherein the antimicrobial agent is silver.

31. A multifilament suture comprising filaments fabricated from biocompatible therapeutic water-soluble glass.

32. A multifilament suture according to claim 31 further comprising filaments of a polymer selected from the group consisting of biocompatible bioabsorbable polymer and biocompatible non-bioabsorbable polymer.

33. A multifilament suture according to claim 31 wherein the multifilament suture is a braided suture.

34. A multifilament suture according to claim 31 wherein the individual filaments are made of a combination of water-soluble glass and a polymer selected from the group consisting of biocompatible bioabsorbable polymer and biocompatible non-bioabsorbable polymer.

35. A multifilament suture according to claim 31 wherein the therapeutic water-soluble glass contains an antimicrobial agent and wherein the antimicrobial agent is silver.

36. A method for preparing a suture having therapeutic activity comprising:
applying to the suture a coating composition including therapeutic water-soluble glass containing a therapeutically effective amount of a therapeutic agent.

37. A method for preparing a suture according to claim 36 wherein the water-soluble glass includes phosphorus pentoxide, sodium oxide and calcium oxide.

38. A method for preparing a suture according to claim 36 wherein the therapeutic agent is silver.

39. A method for preparing a suture according to claim 36 wherein the coating composition includes a biocompatible bioabsorbable polymer.

40. A method for preparing a suture according to claim 39 wherein the bioabsorbable polymer includes:
a) a copolymer including a predominant amount of epsilon-caprolactone and a minor amount of at least one other copolymerizable monomer; and
b) a salt of a lactylate ester of a $C_{10}$ or greater fatty acid selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, zinc palmityl lactylate, calcium olelyl lactylate, magnesium olelyl lactylate, aluminum olelyl lactylate, barium olelyl lactylate, calcium stearoyl lactylate and zinc olelyl lactylate.

41. A method for preparing a suture according to claim 36 wherein the coating composition includes a biocompatible non-bioabsorbable silicon polymer and a crosslinking agent.

42. A method for preparing a suture according to claim 41 further comprising heating the coated suture at a temperature sufficient to cause polymerization of the coating on the suture.

43. A method of preparing a coating composition for a surgical device comprising dispersing therapeutic water-soluble glass and a polymer selected from the group consisting of biocompatible bioabsorbable polymer or biocompatible non-bioabsorbable polymer in a suitable solvent, wherein the coating composition is adapted to coat the surgical device.

44. A method of preparing a coating composition according to claim 43 wherein the non-bioabsorbable polymer is selected from the group consisting of a silicon polymer, a wax and combinations thereof.

45. A method of preparing a coating composition according to claim 43 wherein the non-bioabsorbable polymer is a silicon polymer.

46. A method of preparing a coating composition according to claim 45 wherein silicon polymer further includes a crosslinking agent.

47. A method of preparing a coating composition according to claim 43 wherein the polymer is a bioabsorbable polymer comprising:
a) a copolymer including a predominant amount of epsilon-caprolactone and a minor amount of at least one other copolymerizable monomer; and
b) a salt of a lactylate ester of a $C_{10}$ or greater fatty acid selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, zinc palmityl lactylate, calcium olelyl lactylate, magnesium olelyl lactylate, aluminum olelyl lactylate, barium olelyl lactylate calcium stearoyl lactylate and zinc olelyl lactylate.

48. A method of preparing a coating composition according to claim 47 wherein the therapeutic water-soluble glass contains a silver compound.

49. A method of preparing a coating composition according to claim 48 wherein the silver compound is selected from the group consisting of silver oxide, silver nitrate and silver orthophosphate.

50. A method of preparing a coating composition according to claim 41 wherein the surgical device is a suture or a pledget.

51. A pledget comprising therapeutic water-soluble glass.

52. A pledget according to claim 51 wherein the therapeutic water-soluble glass is contained within the pledget.

53. A pledget according to claim 52 wherein the therapeutic water-soluble glass is coated onto the pledget.

54. A pledget according to claim 51 which is coated with a coating composition comprising a therapeutic water-soluble glass.

55. A pledget according to claim 54 wherein the coating composition further includes a bioabsorbable or non-bioabsorbable polymer.

56. A pledget according to claim 55 wherein the coating composition includes:
   a) a copolymer including a predominant amount of epsilon-caprolactone and a minor amount of at least one other copolymerizable monomer; and
   b) a salt of a lactylate ester of a $C_{10}$ or greater fatty acid selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, zinc palmityl lactylate, calcium olelyl lactylate, magnesium olelyl lactylate, aluminum olelyl lactylate, barium olelyl lactylate, calcium stearoyl lactylate and zinc olelyl lactylate.

57. A pledget according to claim 56 wherein the therapeutic water-soluble glass includes phosphorus pentoxide.

58. A pledget according to claim 57 wherein the therapeutic water-soluble glass further includes sodium oxide and calcium oxide.

59. A pledget according to claim 54 wherein the therapeutic water-soluble glass contains a silver compound.

60. A pledget according to claim 59 wherein the silver compound is selected from the group consisting of silver oxide, silver nitrate and silver orthophosphate.

61. A pledget according to claim 54 wherein the water-soluble glass includes phosphorus pentoxide, sodium oxide, calcium oxide, and a silver compound selected from the group consisting of silver oxide, silver nitrate and silver orthophosphate.

62. A pledget according to claim 54 wherein the pledget comprises a non-woven fabric including fibers of a biocompatible bioabsorbable polymer or a biocompatible nonbioabsorbable polymer.

63. A pledget according to claim 62 wherein the biocompatible bioabsorbable polymer is selected from the group consisting of homopolymers and copolymers of glycolic acid, glycolide, lactide, lactic acid, dioxanone, epsilon-caprolactone, trimethylene carbonate and mixtures thereof.

64. A pledget according to claim 62 wherein the biocompatible non-bioabsorbable polymer is polytetrafluoroethylene.

65. A pledget according to claim 54 wherein the pledget is attached to a suture.

66. A method for preparing a pledget having therapeutic activity comprising: providing therapeutic water-soluble glass;

providing a pledget; and incorporating the therapeutic water-soluble glass into the pledget.

67. A method for preparing a pledget according to claim 66 wherein the water-soluble glass includes phosphorus pentoxide, sodium oxide and calcium oxide.

68. A method for preparing a pledget according to claim 66 wherein the therapeutic agent is silver.

69. A method for preparing a pledget according to claim 66 wherein the pledget is coated with a coating composition, the coating composition including a biocompatible bioabsorbable polymer or a biocompatible non-bioabsorbable polymer.

70. A method for preparing a pledget according to claim 69 wherein the coating composition includes:
   a) a copolymer including a predominant amount of epsilon-caprolactone and a minor amount of at least one other copolymerizable monomer; and
   b) a salt of a lactylate ester of a $C_{10}$ or greater fatty acid selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, zinc palmityl lactylate, calcium olelyl lactylate, magnesium olelyl lactylate, aluminum olelyl lactylate, barium olelyl lactylate, calcium stearoyl lactylate and zinc olelyl lactylate.

71. A method for preparing a pledget according to claim 69 wherein the coating composition comprises a silicon polymer.

72. A method according to claim 66 wherein the therapeutic water-soluble glass is incorporated into the pledget by dipping the pledget in a suspension containing therapeutic water-soluble glass and at least one solvent; and removing the solvent from the pledget.

73. A method according to claim 72 wherein the solvent is selected from the group consisting of methylene chloride, hexanes, ethanol and mixtures thereof.

74. A suture coated with a coating composition according to claim 1.

75. A pledget coated with a coating composition according to claim 1.

* * * * *